US008430294B2

(12) United States Patent
Ho et al.

(10) Patent No.: US 8,430,294 B2
(45) Date of Patent: *Apr. 30, 2013

(54) AMINE, CARBOXYLIC ACID FLUX COMPOSITION AND METHOD OF SOLDERING

(75) Inventors: Kim S. Ho, Richboro, PA (US); Mark R. Winkle, Lansdale, PA (US); Avin V. Dhoble, Waltham, MA (US); Michael K. Gallagher, Hopkinton, MA (US); Xiang-Qian Liu, Collegeville, PA (US); Asghar A. Peera, Cary, IL (US); Glenn N. Robinson, Naperville, IL (US); Ian A. Tomlinson, Midland, MI (US); David Fleming, Northborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/250,184

(22) Filed: Sep. 30, 2011

(65) Prior Publication Data
US 2013/0082093 A1    Apr. 4, 2013

(51) Int. Cl.
*B23K 31/02* (2006.01)
*B23K 35/34* (2006.01)

(52) U.S. Cl.
USPC ...... 228/180.21; 228/207; 228/223; 228/224; 228/248.1; 148/23; 148/24

(58) Field of Classification Search .......... None
See application file for complete search history.

(56) References Cited

U.S. PATENT DOCUMENTS

| | | | |
|---|---|---|---|
| 2,632,022 A | 3/1959 | Bortnick | |
| 2,897,179 A | 7/1959 | Schecter et al. | |
| 3,488,831 A | 1/1970 | Ravve | |
| 3,740,831 A | 6/1973 | Jordan et al. | |
| 3,814,638 A | 6/1974 | Jordan et al. | |
| 3,944,123 A * | 3/1976 | Jacobs | 228/223 |
| 4,028,143 A | 6/1977 | Stayner et al. | |
| 4,165,244 A | 8/1979 | Jacobs | |
| 4,196,024 A | 4/1980 | Kenyon | |
| 4,360,144 A | 11/1982 | Cuddy et al. | |
| RE32,309 E | 12/1986 | Hwang | |
| 5,004,509 A * | 4/1991 | Bristol | 148/23 |
| 5,011,546 A | 4/1991 | Frazier et al. | |
| 5,145,722 A | 9/1992 | Kaspaul | |
| 5,417,771 A * | 5/1995 | Arita et al. | 148/23 |
| 5,531,838 A | 7/1996 | Arldt et al. | |
| 5,571,340 A | 11/1996 | Schneider et al. | |
| 5,863,355 A | 1/1999 | Ohno et al. | |
| 5,932,030 A | 8/1999 | Fukasawa et al. | |
| 5,958,151 A | 9/1999 | Gao et al. | |
| 5,989,362 A | 11/1999 | Diamant et al. | |
| 6,075,080 A * | 6/2000 | Katsuoka et al. | 524/272 |
| 6,217,671 B1 | 4/2001 | Henderson et al. | |
| 6,234,381 B1 | 5/2001 | Hasegawa et al. | |
| 6,367,150 B1 | 4/2002 | Kirsten | |
| 6,746,896 B1 * | 6/2004 | Shi et al. | 438/108 |
| 6,758,389 B1 | 7/2004 | Odaka et al. | |
| 6,887,319 B2 | 5/2005 | Suga et al. | |
| 6,926,849 B2 | 8/2005 | Taguchi et al. | |
| 7,575,150 B2 | 8/2009 | Saito et al. | |
| 2001/0019075 A1 * | 9/2001 | Abe et al. | 228/224 |
| 2001/0045244 A1 | 11/2001 | Akaike et al. | |
| 2002/0190370 A1 | 12/2002 | Shi et al. | |
| 2003/0051770 A1 * | 3/2003 | Nishina et al. | 148/23 |
| 2003/0111519 A1 | 6/2003 | Kinney et al. | |
| 2003/0159761 A1 | 8/2003 | Ikeda et al. | |
| 2004/0026484 A1 * | 2/2004 | Yamashita et al. | 228/180.22 |
| 2005/0067395 A1 | 3/2005 | Shindo et al. | |
| 2005/0131106 A1 | 6/2005 | Tonapi et al. | |
| 2005/0170188 A1 | 8/2005 | Campbell et al. | |
| 2006/0068521 A1 * | 3/2006 | Shi et al. | 438/108 |
| 2006/0102691 A1 | 5/2006 | Toyama et al. | |
| 2006/0147683 A1 | 7/2006 | Ikeda et al. | |
| 2006/0272747 A1 | 12/2006 | Wang et al. | |
| 2006/0275608 A1 | 12/2006 | Tonapi et al. | |
| 2007/0241170 A1 | 10/2007 | Ikeda et al. | |
| 2007/0277373 A1 | 12/2007 | Takai et al. | |
| 2008/0023108 A1 | 1/2008 | Wang et al. | |
| 2008/0124568 A1 | 5/2008 | Duchesne et al. | |
| 2008/0156852 A1 | 7/2008 | Prakash | |
| 2008/0179383 A1 | 7/2008 | Sakurai et al. | |
| 2009/0018239 A1 | 1/2009 | Woods et al. | |
| 2009/0320960 A1 * | 12/2009 | Nishina et al. | 148/24 |
| 2010/0143658 A1 | 6/2010 | Lawrence | |
| 2010/0175790 A1 | 7/2010 | Duchesne et al. | |
| 2011/0100512 A1 | 5/2011 | Bedard et al. | |

FOREIGN PATENT DOCUMENTS
DE            2828197 A   *   1/1980

OTHER PUBLICATIONS

Copending U.S. Appl. No. 12/958,495.
Copending U.S. Appl. No. 12/958,487.
Copending U.S. Appl. No. 12/958,480.
Copending U.S. Appl. No. 12/958,493.
Copending U.S. Appl. No. 12/958,473.
Copending U.S. Appl. No. 13/250,226.
Copending U.S. Appl. No. 13/250,007.
Copending U.S. Appl. No. 13/250,297.
Copending U.S. Appl. No. 13/250,125.

* cited by examiner

Primary Examiner — Kiley Stoner
(74) Attorney, Agent, or Firm — Thomas S. Deibert

(57) ABSTRACT

A flux composition is provided, comprising, as initial components: a carboxylic acid; and, an amine fluxing agent represented by formula I:

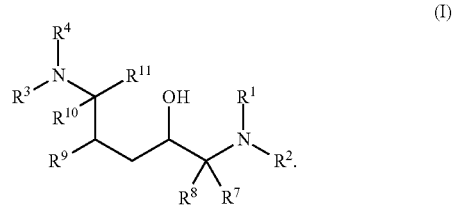

Also provided is a method of soldering an electrical contact using the flux composition.

10 Claims, No Drawings

AMINE, CARBOXYLIC ACID FLUX COMPOSITION AND METHOD OF SOLDERING

The present invention relates to a flux composition comprising, as initial components: a carboxylic acid; and, an amine fluxing agent represented by formula I, wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group. The present invention further relates to a method of soldering an electrical contact.

Soldering processes ranging from manual, hand soldering methods to automated soldering methods. The use of flux materials in soldering processes, both manual and automated, is also well know. In fact, the use of solder alone generally will not result in an acceptable electrical interconnection. Flux materials serve multiple functions in the soldering process. For example, flux materials operate to remove any oxides that may have formed on the metallic contacts (e.g., solder regions, contact pads, contact pins, copper plated through holes); to enhance wetting of solder onto the metallic contacts.

Various methods have been employed to apply flux materials to the surface of a metallic contact during the soldering process. In some methods, flux materials containing solder are used. For example, such combined materials have been provided in the form of an annular shaped wire incorporating a core of flux material. As the solder melts upon heating, the flux material in the core is activated, fluxing the surfaces to be interconnected by the molten solder. Solder pastes are also known in which a flux material and a solder powder are compounded to form a generally homogenous stable suspension of solder particles in the paste.

One commercially significant, application of an automated soldering method is the manufacture of semiconductor devices. That is, reflow soldering processes are commonly used in the automated production of semiconductor devices, wherein a semiconductor chip is mounted on to a printed circuit board (PCB). In some such automated production methods, a solder paste is applied to a printed circuit board using, for example, screen printing or stencil printing. The semiconductor chip is then brought into contact with the PCB and the solder paste is heated to reflow the solder in the paste, forming electrical interconnects between the semiconductor chip and the PCB. The heating may be facilitated by, for example, exposure of the solder paste to infrared light or by heating in an oven. In some applications, the semiconductor chip/PCB assembly is further treated with an under fill material that substantially fills the interstitial area between the semiconductor chip and the PCB, encapsulating the interconnects.

Given the demands for the mass production of electronic devices containing circuits of increasing complexity and miniaturization, rapid, automated soldering processes have emerged, such as, for example, those incorporating pick and dip processes. In such processes, a flux can be applied to a plurality of electrical contacts on a semiconductor chip by dipping the electrical contact portion of the semiconductor chip into a bath of flux. The flux coated electrical contacts on the semiconductor chip can then be brought into contact with a PCB comprising corresponding electrical contacts and solder balls. The solder balls may then be heated to reflux interconnecting the semiconductor chip and the PCB. Alternatively, the pick and dip process can be employed with device components that have electrical contacts with preapplied solder. In these processes, the preapplied solder is dip coated with the flux material and then brought into contact with the corresponding electrical contact(s) and heated to reflow, forming the electrical interconnects. Many electronic components fit into this latter process category in that they are manufactured with a sufficient amount of solder on board the component to facilitate interconnection of the component with another electrical component (e.g., a PCB).

In most instances, use of commercially available fluxes leave ionic residues on the soldered regions, which may undesirably lead to corrosion of circuitry and to short circuits. Accordingly, additional process steps are required to remove such residues after formation of the soldered interconnections. For semiconductor device manufacturing processes, the solder connections formed between the semiconductor chip and the PCB result in a relatively small gap between the semiconductor chip and the PCB (e.g., <4 mils). Hence, it is very difficult to remove (i.e., clean) ionic residues remaining on the soldered regions following the soldering process. Even in processes where the soldered regions are accessible (hence, facilitating cleaning operations), cleaning operations create environmental concerns involving the disposal of the waste generated during the cleaning operations.

Some low residue, no clean fluxes having a low solid content are commercially available. One flux composition asserted to substantially minimize or substantially eliminate flux residues when soldering electronic components is disclosed in U.S. Patent Application Publication No. 20100175790 to Duchesne et al. Duchesne et al. disclose a composition of matter comprising a flux, wherein said flux consists essentially of a combination of: (a) a fluxing agent; and (b) a solvent; wherein said fluxing agent: (1) comprises a keto acid; or (2) comprises an ester acid; or (3) comprises a mixture of said keto acid with said ester acid; and wherein said solvent comprises a mixture of a tacky solvent selected from polyhydric alcohols or mixtures thereof, and a non-tacky solvent selected from monohydric alcohols or mixtures thereof.

Notwithstanding, there remains a need for flux compositions that are non-curing, facilitate reliable soldering connections and are customizable to facilitate compatibility with conventional epoxy based under fill materials.

The present invention provides a flux composition comprising, as initial components: a carboxylic acid; and, an amine fluxing agent represented by formula I:

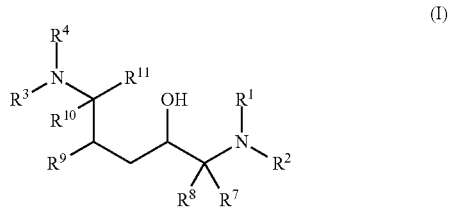

wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group.

The present invention provides a method of applying solder to an electrical contact, comprising: providing an electrical contact; providing a flux composition of the present invention; applying the flux composition to the electrical contact; providing a solder; melting the solder; and, displacing the flux composition applied to the electrical contact with the molten solder; wherein the molten solder makes physical contact with the electrical contact and bonds to the electrical contact.

DETAILED DESCRIPTION

The flux composition of the present invention is designed to facilitate compatibilization with various under fill compositions, such that, the soldered surfaces preferably do not require cleaning before application of an under fill composition to form a finished electrical joint.

The term "no clean flux composition" as used herein and in the appended claims refers to flux compositions that exhibit a low, or no, flux residue activity with <0.5 wt % halide content (i.e., fluxes that are categorized as an ORL1 or ORL0 under IPC J-STD-004B).

The flux composition of the present invention comprises (consists essentially of), as initial components: a carboxylic acid; and, an amine fluxing agent represented by formula I. Preferably, the flux composition is a non-curing composition (i.e., wherein the flux composition is free of compounds having two or more reactive functional groups per molecule capable of reacting under soldering conditions to form inter molecular covalent bonds and wherein the amine fluxing agent does not contain two or more reactive functional groups per molecule capable of reacting under soldering conditions to form inter molecular covalent bonds).

Preferably, the carboxylic acid used in the flux composition of the present invention, is selected from $C_{8-20}$ aliphatic mono carboxylic acids; $C_{2-20}$ aliphatic dicarboxylic acids; $C_{6-20}$ aromatic carboxylic acids; and, mixtures thereof. More preferably, the carboxylic acid used in the flux composition of the present invention is selected from octanoic acid; nonanioc acid; undecanoic acid; dodecanoic acid; tridecanoic acid; tetradecanoic acid; pentadecanoic acid; hexadecanoic acid; heptadecanoic acid; stearic acid; hydroxy stearic acid; oleic acid; linoleic acid; α-linolenic acid; icosanoic acid; oxalic acid; malonic acid; succinic acid; malic acid; glutaric acid; adipic acid; pimelic acid; suberic acid; benzoic acid; phthalic acid; isophthalic acid; terephthalic acid; hemimellitic acid; trimellitic acid; trimesic acid; mellophanic acid; prehnitic acid; pyromellitic acid; mellitic acid; toluic acid; xylic acid; hemellitic acid; mesitylene acid; prehnitic acid; cinnamic acid; salicylic acid; benzoic acid (e.g., benzoic acid; 2,3-dihydroxybenzoic acid; 2,4-dihydroxybenzoic acid; 2,5-dihydroxybenzoic acid (gentisic acid); 2,6-dihydroxybenzoic acid; 3,5-dihydroxybenzoic acid; 3,4,5-trihydroxybenzoic acid (gallic acid)); naphthoic acid (e.g., naphthoic acid; 1,4-dihydroxy-2-naphthoic acid; 3,5-dihydroxy-2-naphthoic acid; 3,7-dihydroxy-2-naphthoic acid); phenolphthalin; diphenolic acid and mixtures thereof. Still more preferably, the carboxylic acid used in the flux composition of the present invention is selected from naphthoic acid (e.g., naphthoic acid; 1,4-dihydroxy-2-naphthoic acid; 3,5-dihydroxy-2-naphthoic acid; 3,7-dihydroxy-2-naphthoic acid), stearic acid; hydroxy stearic acid; oleic acid; linoleic acid; α-linolenic acid; and icosanoic acid; and, mixtures thereof. Yet still more preferably, the carboxylic acid used in the flux composition of the present invention is selected from naphthoic acid (e.g., naphthoic acid; 1,4-dihydroxy-2-naphthoic acid; 3,5-dihydroxy-2-naphthoic acid; 3,7-dihydroxy-2-naphthoic acid), stearic acid; hydroxy stearic acid; oleic acid; and, mixtures thereof. Most preferably, the carboxylic acid used in the flux composition of the present invention is selected from naphthoic acid, a $C_{18}$ carboxylic acid and mixtures thereof; wherein the naphthoic acid is selected from 1,4-dihydroxy-2-naphthoic acid; 3,5-dihydroxy-2-naphthoic acid; and the $C_{18}$ carboxylic acid is selected from stearic acid, hydroxy stearic acid, and oleic acid.

The amine fluxing agent used in the flux composition of the present invention is according to formula I, wherein $R^1$, $R^2$, $R^3$ and $R^4$ are independently selected from hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group (preferably wherein $R^1$, $R^2$, $R^3$ and $R^4$ are independently selected from a hydrogen, a substituted $C_{1-20}$ alkyl group, an unsubstituted $C_{1-20}$ alkyl group, a substituted $C_{7-30}$ arylalkyl group and an unsubstituted $C_{7-30}$ arylalkyl group); wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group (alternatively, wherein $R^7$ and $R^8$, together with the carbon to which they are attached, form a $C_{3-20}$ cycloalkyl ring optionally substituted with a $C_{1-6}$ alkyl group); wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group (alternatively, wherein $R^{10}$ and $R^{11}$, together with the carbon to which they are attached, form a $C_{3-20}$ cycloalkyl ring optionally substituted with a $C_{1-6}$ alkyl group); and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group. Preferably, zero to three of $R^1$, $R^2$, $R^3$ and $R^4$ is(are) hydrogen. The $R^1$, $R^2$, $R^3$, $R^4$, $R^7$, $R^8$, $R^9$, $R^{10}$ and $R^{11}$ groups of the amine fluxing agent according to formula I are preferably selected: to provide the amine fluxing agent with desirable rheological properties for a given application; to facilitate the formation of the fluxing complex with the carboxylic acid; optionally, to compatibilize the amine fluxing agent with a given solvent package for delivery to the surface(s) to be soldered; and, optionally, to compatibilize the amine fluxing agent with a given encapsulating composition (e.g., an epoxy resin) to be used post soldering to form an encapsulated solder joint (e.g., for use in conventional flip chip under fill applications). Preferably, the $R^1$, $R^2$, $R^3$, $R^4$, $R^7$, $R^8$, $R^9$, $R^{10}$ and $R^{11}$ groups of the amine fluxing agent according to formula I are selected to compatibilize the amine fluxing agent with a given encapsulating composition such that the flux composition is a no clean flux composition. Preferably, zero to three of $R^1$, $R^2$, $R^3$ and $R^4$ is(are) a hydrogen. More preferably, one to three of $R^1$, $R^2$, $R^3$ and $R^4$ is(are) a hydrogen. Still more preferably, two to three of $R^1$, $R^2$, $R^3$ and $R^4$ are a hydrogen. Yet still more preferably, two of $R^1$, $R^2$, $R^3$ and $R^4$ are a hydrogen. Most preferably, one of $R^1$ and $R^2$ is a hydrogen and one of $R^3$ and $R^4$ is a hydrogen. Also, the $R^1$, $R^2$, $R^3$, $R^4$, $R^7$, $R^8$, $R^9$, $R^{10}$ and $R^{11}$ groups of the amine fluxing agent according to formula I are preferably selected to provide the amine fluxing agent with a boiling point temperature, determined by differential scanning calorimetry of ≧125° C. (more preferably ≧250° C.) and a percent weight loss of ≦10 wt % upon heating to 250° C. determined by thermogravimetric analysis (TGA) using a temperature ramp of 10° C./min starting at 25° C.

Preferably, the amine fluxing agent used in the amine fluxing composition of the present invention is according to formula I; wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; and, wherein the substitutions in the substituted $C_{1-80}$ alkyl group and the substituted $C_{7-80}$ arylalkyl group are selected from at least one of an —OH group, an —OR$^5$ group, a —COR$^5$-group, a —COR$^5$ group, a —C(O)R$^5$ group, a —CHO group, a —COOR$^5$ group, an —OC(O)OR$^5$ group, a —S(O)(O)R$^5$ group, a —S(O)R$^5$ group, a —S(O)(O)NR$^5_2$ group, an —OC(O)NR$^6_2$ group, a —C(O)NR$^6_2$ group, a —CN group, a —N(R$^6$)-group and a —NO$_2$ group (preferably at least one of an —OH group, an —OR$^5$ group, a —COR$^5$-group, a —COR$^5$ group, a —C(O)R$^5$ group, a —CHO group, a —COOR$^5$ group, an —OC(O)OR$^5$ group, a —S(O)(O)R$^5$ group, a —S(O)R$^5$ group, a —S(O)(O)NR$^5_2$ group, an —OC(O)NR$^6_2$ group, a —C(O)NR$^6_2$ group, a —CN group and a —NO$_2$ group); wherein $R^5$ is selected from a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group; wherein $R^6$ is selected from a hydrogen, a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group. The substituted $C_{1-80}$ alkyl group and the substituted $C_{7-80}$ arylalkyl group can contain combinations of substitutions. For example, the substituted $C_{1-80}$ alkyl group and the substituted $C_{7-80}$ arylalkyl group can: contain more than one of the same type of substitution (e.g., two —OH groups); contain more than one type of substitution (e.g., an —OH group and a —COR$^5$-group); contain more than one type of substitution with more than one of the same type of substitution (e.g., two —OH groups and an —OR$^5$ group).

Preferably, the amine fluxing agent used in the amine fluxing composition of the present invention is according to formula I; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group (alternatively, wherein $R^7$ and $R^8$, together with the carbon to which they are attached, form a $C_{3-20}$ cycloalkyl ring optionally substituted with a $C_{1-6}$ alkyl group); and wherein the substitutions in the substituted $C_{1-20}$ alkyl group and the substituted $C_{6-20}$ aryl group are selected from at least one of an —OH group, a phenyl group, a $C_{1-14}$ alkyl group, an —OR$^{12}$ group, a —COR$^{12}$-group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{13}_2$ group, an —OC(O)NR$^{13}_2$ group, a —C(O)NR$^{13}_2$ group, a —CN group, a —N(R$^{13}$)-group and a —NO$_2$ group (preferably at least one of an —OH group, an —OR$^{12}$ group, a —COR$^{12}$-group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{12}_2$ group, an —OC(O)NR$^{13}_2$ group, a —C(O)NR$^{13}_2$ group, a —CN group and a —NO$_2$ group); wherein $R^{12}$ is selected from a $C_{1-19}$ alkyl group, a $C_{3-19}$ cycloalkyl group, a $C_{6-19}$ aryl group, a $C_{7-19}$ arylalkyl group and a $C_{7-19}$ alkylaryl group; and wherein $R^{13}$ is selected from a hydrogen, a $C_{1-19}$ alkyl group, a $C_{3-19}$ cycloalkyl group, a $C_{6-19}$ aryl group, a $C_{7-19}$ arylalkyl group and a $C_{7-19}$ alkylaryl group. The substituted $C_{1-20}$ alkyl group and the substituted $C_{6-20}$ aryl group can contain combinations of substitutions. For example, the substituted $C_{1-20}$ alkyl group and the substituted $C_{6-20}$ aryl group can: contain more than one of the same type of substitution (e.g., two —OH groups); contain more than one type of substitution (e.g., an —OH group and a —COR$^{12}$-group); contain more than one type of substitution with more than one of the same type of substitution (e.g., two —OH groups and an —OR$^{12}$ group).

Preferably, the amine fluxing agent used in the amine fluxing composition of the present invention is according to formula I; wherein $R^{10}$ and $R^{11}$ are independently selected from a $C_{6-20}$ alkyl group, a substituted $C_{1-20}$ alkyl group, a $C_{6-20}$ aryl group and a substituted $C_{6-20}$ aryl group (alternatively, wherein $R^{10}$ and $R^{11}$, together with the carbon to which they are attached, form a $C_{3-20}$ cycloalkyl ring optionally substituted with a $C_{1-6}$ alkyl group); and, wherein the substitutions in the substituted $C_{1-20}$ alkyl group and the substituted $C_{6-20}$ aryl group are selected from at least one of an —OH group, an —OR$^{12}$ group, a —COR$^{12}$-group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{12}_2$ group, an —OC(O)NR$^{13}_2$ group, a —C(O)NR$^{13}_2$ group, a —CN group, a —N(R$^{13}$)-group and a —NO$_2$ group (preferably at least one of an —OH group, an —OR$^{12}$ group, a —COR$^{12}$-group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{12}_2$ group, an —OC(O)NR$^{13}_2$ group, a —C(O)NR$^{13}_2$ group, a —CN group and a —NO$_2$ group); wherein $R^{12}$ is selected from a $C_{1-19}$ alkyl group, a $C_{3-19}$ cycloalkyl group, a $C_{6-19}$ aryl group, a $C_{7-19}$ arylalkyl group and a $C_{7-19}$ alkylaryl group; and wherein $R^{13}$ is selected from a hydrogen, a $C_{1-19}$ alkyl group, a $C_{3-19}$ cycloalkyl group, a $C_{6-19}$ aryl group, a $C_{7-19}$ arylalkyl group and a $C_{7-19}$ alkylaryl group. The substituted $C_{1-20}$ alkyl group and the substituted $C_{6-20}$ aryl group can contain combinations of substitutions. For example, the substituted $C_{1-20}$ alkyl group and the substituted $C_{6-20}$ aryl group can: contain more than one of the same type of substitution (e.g., two —OH groups); contain more than one type of substitution (e.g., an —OH group and a —COR$^{12}$-group); contain more than one type of substitution with more than one of the same type of substitution (e.g., two —OH groups and an —OR$^{12}$ group).

Preferably, the amine fluxing agent used in the flux composition of the present invention is according to formula I; wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group; and, wherein the substitutions in the substituted $C_{1-30}$ alkyl group and the substituted $C_{6-30}$ aryl group are selected from at least one of an —OH group, an —OR$^{14}$ group, a —COR$^{14}$- group, a —COR$^{14}$ group, a —C(O)R$^{14}$ group, a —CHO group, a —COOR$^{14}$ group, an —OC(O)OR$^{14}$ group, a —S(O)(O)R$^{14}$ group, a —S(O)R$^{14}$ group, a —S(O)(O)NR$^{14}_2$ group, an —OC(O)NR$^{15}_2$ group, a —C(O)NR$^{15}_2$ group, a —CN group, a —N(R$^{15}$)-group and a —NO$_2$ group (preferably at least one of an —OH group, an —OR$^{14}$ group, a —COR$^{14}$-group, a —COR$^{14}$ group, a —C(O)R$^{14}$ group, a —CHO group, a —COOR$^{14}$ group, an —OC(O)OR$^{14}$ group, a —S(O)(O)R$^{14}$ group, a —S(O)R$^{14}$ group, a —S(O)(O)NR$^{14}_2$ group, an —OC(O)NR$^{15}_2$ group, a —C(O)NR$^{15}_2$ group, a —CN group and a —NO$_2$ group); wherein $R^{14}$ is selected from a $C_{1-29}$ alkyl group, a $C_{3-29}$ cycloalkyl group, a $C_{6-29}$ aryl group, a $C_{7-29}$ arylalkyl group and a $C_{7-29}$ alkylaryl group; and wherein $R^{15}$ is selected from a hydrogen, a $C_{1-29}$ alkyl group, a $C_{3-29}$ cycloalkyl group, a $C_{6-29}$ aryl group, a $C_{7-29}$ arylalkyl group and a $C_{7-29}$ alkylaryl group. The substituted $C_{1-30}$ alkyl group and the substituted $C_{6-30}$ aryl group can contain combinations of substitutions. For example, the substituted $C_{1-30}$ alkyl group and the substituted $C_{6-30}$ aryl group can: contain more than one of the same type of substitution (e.g., two —OH groups); contain more than one type of substitution (e.g., an —OH group and a —$COR^{14}$-group); contain more than one type of substitution with more than one of the same type of substitution (e.g., two —OH groups and an —$OR^{14}$ group).

More preferably, the amine fluxing agent used in the flux composition of the present invention is according to formula I; wherein $R^1$, $R^2$, $R^3$ and $R^4$ are independently selected from a hydrogen, a substituted $C_{1-20}$ alkyl group, an unsubstituted $C_{1-20}$ alkyl group, a substituted $C_{7-30}$ arylalkyl group and an unsubstituted $C_{7-30}$ arylalkyl group; and, wherein the substitutions in the substituted $C_{1-20}$ alkyl group and the substituted $C_{7-30}$ arylalkyl group are selected from at least one of an —OH group, an —$OR^{16}$ group, a —$COR^6$-group, a —$COR^{16}$ group, a —$C(O)R^{16}$ group, a —CHO group, a —$COOR^{16}$ group, an —$OC(O)OR^{16}$ group, a —$S(O)(O)R^{16}$ group, a —$S(O)R^{16}$ group, a —$S(O)(O)NR^{16}{}_2$ group, an —$OC(O)NR^{17}{}_2$ group, a —$C(O)NR^{17}{}_2$ group, a —CN group, a —$N(R^{17})$-group and a —$NO_2$ group (preferably at least one of an —OH group, an —$OR^{16}$ group, a —$COR^{16}$-group, a —$COR^{16}$ group, a —$C(O)R^{16}$ group, a —CHO group, a —$COOR^{16}$ group, an —$OC(O)OR^{16}$ group, a —$S(O)(O)R^{16}$ group, a —$S(O)R^{16}$ group, a —$S(O)(O)NR^{16}{}_2$ group, an —$OC(O)NR^{17}{}_2$ group, a —$C(O)NR^{17}{}_2$ group, a —CN group and a —$NO_2$ group); wherein $R^{16}$ is selected from a $C_{1-19}$ alkyl group, a $C_{3-19}$ cycloalkyl group, a $C_{6-15}$ aryl group, a $C_{7-19}$ arylalkyl group and a $C_{7-19}$ alkylaryl group; wherein $R^{17}$ is selected from a hydrogen, a $C_{1-19}$ alkyl group, a $C_{3-19}$ cycloalkyl group, a $C_{6-15}$ aryl group, a $C_{7-19}$ arylalkyl group and a $C_{7-19}$ alkylaryl group; wherein $R^7$ and $R^8$ are independently selected from a $C_{1-4}$ alkyl group and a $C_{1-4}$ hydroxy alkyl group (more preferably wherein $R^7$ and $R^8$ are independently selected from a methyl group and a hydroxy methyl group; most preferably wherein $R^7$ and $R^8$ are both a methyl group); wherein $R^{10}$ and $R^{11}$ are independently selected from a $C_{1-4}$ alkyl group and a $C_{1-4}$ hydroxy alkyl group (more preferably wherein $R^{10}$ and $R^{11}$ are independently selected from a methyl group and a hydroxy methyl group; most preferably wherein $R^{10}$ and $R^{11}$ are both a methyl group); and, wherein $R^9$ is selected from a hydrogen, a $C_{1-10}$ alkyl group, a $C_{1-10}$ hydroxyalkyl group, a phenyl group, a hydroxyphenyl group, a $C_{7-10}$ alkylaryl group, a $C_{7-10}$ arylalkyl group and a naphthyl group (more preferably wherein $R^9$ is selected from a hydrogen, a $C_{1-4}$ alkyl group, a $C_{1-4}$ hydroxyl alkyl group, a phenyl group, a hydroxyl phenyl group, a $C_7$ alkylaryl group and a $C_7$ arylalkyl group; most preferably wherein $R^9$ is selected from a methyl group and a phenyl group). The substituted $C_{1-20}$ alkyl group and the substituted $C_{7-30}$ arylalkyl group, from which $R^1$, $R^2$, $R^3$ and $R^4$ are selected, can contain combinations of substitutions. For example, the substituted $C_{1-20}$ alkyl group and the substituted $C_{7-30}$ arylalkyl group can: contain more than one of the same type of substitution (e.g., two —OH groups); contain more than one type of substitution (e.g., an —OH group and a —$COR^{16}$-group); contain more than one type of substitution with more than one of the same type of substitution (e.g., two —OH groups and an —$OR^{16}$ group). Preferably, zero to three of $R^1$, $R^2$, $R^3$ and $R^4$ is(are) a hydrogen. More preferably, one to three of $R^1$, $R^2$, $R^3$ and $R^4$ is(are) a hydrogen. Still more preferably, two to three of $R^1$, $R^2$, $R^3$ and $R^4$ are a hydrogen. Yet still more preferably, two of $R^1$, $R^2$, $R^3$ and $R^4$ are a hydrogen. Most preferably, one of $R^1$ and $R^2$ is a hydrogen and one of $R^3$ and $R^4$ is a hydrogen.

Still more preferably, the amine fluxing agent used in the flux composition of the present invention is according to formula I; wherein $R^1$, $R^2$, $R^3$ and $R^4$ are independently selected from a hydrogen, a —$CH_2CH(OH)R^{18}$ and a —$CH_2CH(OH)CH_2$—)—$R^{18}$ group; wherein $R^{18}$ is selected from a hydrogen, a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group (preferably, wherein $R^{18}$ is selected from a $C_{5-10}$ alkyl group, a $C_{6-15}$ aryl group and a $C_{7-15}$ alkylaryl group; most preferably wherein $R^{18}$ is selected from a $C_8$ alkyl group, a $C_7$ alkylaryl group and a $C_{10}$ naphthyl group); wherein $R^7$ and $R^8$ are independently selected from a $C_{1-4}$ alkyl group and a $C_{1-4}$ hydroxy alkyl group (more preferably wherein $R^7$ and $R^8$ are independently selected from a methyl group and a hydroxy methyl group; most preferably wherein $R^7$ and $R^8$ are both a methyl group); wherein $R^{10}$ and $R^{11}$ are independently selected from a $C_{1-4}$ alkyl group and a $C_{1-4}$ hydroxy alkyl group (more preferably wherein $R^{10}$ and $R^{11}$ are independently selected from a methyl group and a hydroxy methyl group; most preferably wherein $R^{10}$ and $R^{11}$ are both a methyl group); and, wherein $R^9$ is selected from a hydrogen, a $C_{1-10}$ alkyl group, a $C_{1-10}$ hydroxyalkyl group, a phenyl group, a hydroxyphenyl group, a $C_{7-10}$ alkylaryl group, a $C_{7-10}$ arylalkyl group and a naphthyl group (more preferably wherein $R^9$ is selected from a hydrogen, a $C_{1-4}$ alkyl group, a $C_{1-4}$ hydroxyl alkyl group, a phenyl group, a hydroxyl phenyl group, a $C_7$ alkylaryl group and a $C_7$ arylalkyl group; most preferably wherein $R^9$ is selected from a methyl group and a phenyl group). Preferably, zero to three of $R^1$, $R^2$, $R^3$ and $R^4$ is(are) a hydrogen. More preferably, one to three of $R^1$, $R^2$, $R^3$ and $R^4$ is(are) a hydrogen. Still more preferably, two to three of $R^1$, $R^2$, $R^3$ and $R^4$ are a hydrogen. Yet still more preferably, two of $R^1$, $R^2$, $R^3$ and $R^4$ are a hydrogen. Most preferably, one of $R^1$ and $R^2$ is a hydrogen and one of $R^3$ and $R^4$ is a hydrogen.

Most preferably, the amine fluxing agent used in the flux composition of the present invention is according to formula I; wherein $R^1$, $R^2$, $R^3$ and $R^4$ are independently selected from a hydrogen, a —$CH_2CH(OH)R^{18}$ and a —$CH_2CH(OH)CH_2$—O—$R^{18}$ group; wherein $R^{18}$ is selected from a hydrogen, a —$CH_2CH(OH)R^{18}$ and a —$CH_2CH(OH)CH_2$—O—$R^8$ group; wherein $R^{18}$ is selected from a hydrogen, a $C_{1-28}$ alkyl group, a $C_{3-28}$ cycloalkyl group, a $C_{6-16}$ aryl group, a $C_{7-28}$ arylalkyl group and a $C_{7-28}$ alkylaryl group (preferably, wherein $R^{18}$ is selected from a $C_{5-10}$ alkyl group, a $C_{6-16}$ aryl group and a $C_{7-15}$ alkylaryl group; more preferably wherein $R^{18}$ is selected from a $C_8$ alkyl group, a $C_7$ alkylaryl group, a naphthyl group, a biphenyl group and a substituted $C_{12-16}$ biphenyl group; most preferably, wherein $R^{18}$ is selected from a $C_8$ alkyl group, a $C_7$ alkylaryl group and a naphthyl group); wherein $R^7$ and $R^8$ are both a methyl group; wherein $R^{10}$ and $R^{11}$ are both a methyl group; and, wherein $R^9$ is selected a methyl group and a phenyl group. Preferably, zero to three of $R^1$, $R^2$, $R^3$ and $R^4$ is(are) a hydrogen. More preferably, one to three of $R^1$, $R^2$, $R^3$ and $R^4$ is(are) a hydrogen. Still more preferably, two to three of $R^1$, $R^2$, $R^3$ and $R^4$ are a hydrogen. Yet still more preferably, two of $R^1$, $R^2$, $R^3$ and $R^4$ are a hydrogen. Most preferably, $R^1$ and $R^3$ are a hydrogen; and, $R^2$ and $R^4$ are selected from a —$CH_2CH(OH)R^{18}$ and a —$CH_2CH(OH)CH_2$—O—$R^{18}$ group.

Preferably, the flux composition of the present invention comprises, as initial components: a carboxylic acid and an amine fluxing agent represented by formula I at an amine fluxing agent amine nitrogen to carboxylic acid acid content (—COOH) equivalent ratio of 1:1 to 20:1 (more preferably, 1:1 to 10:1; most preferably, 1:1 to 4:1). Preferably, when combined, the carboxylic acid and the amine fluxing agent represented by formula I, form a fluxing complex. Preferably, the fluxing complex formed is an acid-base complex. Preferably, the fluxing complex exhibits a percent weight loss of ≦25 wt % (more preferably ≦20 wt %; most preferably ≦15 wt %) upon heating to 230° C. determined by thermogravimetric analysis (TGA) using a temperature ramp of 10° C./min starting at 25° C.

The flux composition of the present invention optionally further comprises a solvent. Solvent is optionally included in the flux composition of the present invention to facilitate delivery of the amine fluxing agent to the surface, or surfaces, to be soldered. Preferably, the flux composition contains 8 to 95 wt % solvent. Solvent used in the flux composition of the present invention is preferably an organic solvent selected from hydrocarbons (e.g., dodecane, tetradecane); aromatic hydrocarbons (e.g., benzene, toluene, xylene, trimethylbenzene, butyl benzoate, dodecylbenzene); ketones (e.g., methyl ethyl ketone, methyl isobutyl ketone, cyclohexanone); ethers (e.g., tetrahydrofuran, 1,4-dioxaneandtetrahydrofuran, 1,3-dioxalane, diprolylene glycol dimethyl ether); alcohols (e.g., 2-methoxy-ethanol, 2-butoxyethanol, methanol, ethanol, iso-propanol, α-terpineol, benzyl alcohol, 2-hexyldecanol,); esters (e.g., ethyl acetate, ethyl lactate, butyl acetate, diethyl adipate, diethyl phthalate, diethylene glycol monobutyl acetate, ethyl lactate, methyl 2-hydroxyisobutyrate, propylene glycol monomethyl ether acetate); and, amides (e.g., N-methylpyrrolidone, N,N-dimethylformamide and N,N-dimethylacetamide); glycol derivatives (e.g., cellosolve, butyl cellosolve); glycols (e.g., ethylene glycol; diethylene glycol; dipropylene glycol; triethylene glycol; hexylene glycol; 1,5-pentanediol); glycol ethers (e.g., propylene glycol monomethyl ether, methyl carbitol, butyl carbitol, triethylene glycol monomethyl ether, triethylene glycol dimethyl ether, tetraethylene glycol dimethyl ether, diethylene glycol monomethyl ether, diethylene glycol monobutyl ether, diethylene glycol monohexyl ether, ethylene glycol monophenyl ether, diethylene glycol monophenyl ether, diethylene glycol-2-ethylhexyl ether,); and petroleum solvents (e.g., petroleum ether, naptha). More preferably, the solvent used in the flux composition of the present invention is an organic solvent selected from methyl ethyl ketone; 2-propanol; propylene glycol monomethyl ether; propylene glycol monomethyl ether acetate; ethyl lactate and methyl 2-hydroxy isobutyrate. Most preferably, the solvent used in the flux composition of the present invention is propylene glycol monomethyl ether.

The flux composition of the present invention optionally further comprises a thickening agent. Preferably, the flux composition contains 0 to 30 wt % thickening agent. Thickening agent used in the flux composition of the present invention can be selected from non-curing resin materials (i.e., <2 reactive functional groups per molecule), such as, for example, a non-curing novolac resin.

The flux composition of the present invention optionally further comprises a thixotropic agent. Preferably, the flux composition contains 1 to 30 wt % thixotropic agent. Thixotropic agent used in the flux composition of the present invention can be selected from fatty acid amides (e.g., stearamide, hydroxystearic acid bisamide); fatty acid esters (e.g., castor wax, beeswax, carnauba wax); organic thixotropic agents (e.g., polyethylene glycol, polyethylene oxide, methyl cellulose, ethyl cellulose, hydroxyethyl cellulose, hydroxypropyl cellulose, diglycerine monooleate, deglycerine laurate, decaglycerine oleate, diglycerine monolaurate, sorbitan laurate); inorganic thixotropic agents (e.g., silica powders, kaolin powders). Preferably, the thixotropic agent used is selected from a polyethylene glycol and a fatty acid amide.

The flux composition of the present invention optionally further comprise an inorganic filler. Inorganic fillers can be selected from alumina, aluminum hydroxide, aluminosilicate, cordierite, lithium aluminum silicate, magnesium aluminate, magnesium hydroxide, clay, talc, antimony trioxide, antimony pentoxide, zinc oxide, colloidal silica, fused silica, glass powder, quartz powder and glass microspheres.

The flux composition of the present invention optionally further comprises an antioxidant. Preferably, the flux composition of the present invention contains 0.01 to 30 wt % antioxidant.

The flux composition of the present invention optionally further comprises an additive selected from matting agents, coloring agents, defoaming agents, dispersion stabilizers, chelating agents, thermoplastic particles, UV impermeable agents, flame retardants, leveling agents, adhesion promoters and reducing agents.

The flux composition of the present invention preferably comprises (consists essentially of), as an initial component: 3.99 to 100 wt % of a fluxing complex formed by the combination of a carboxylic acid with an amine fluxing agent represented by formula I. Preferably, the flux composition of the present invention comprises (consists essentially of), as initial components: 3.99 to 100 wt % of a fluxing complex formed by the combination of a carboxylic acid and an amine fluxing agent represented by formula I, 0 to 95 wt % (more preferably 8 to 95 wt %) of a solvent, 0 to 30 wt % thickening agent, 0 to 30 wt % (more preferably 1 to 30 wt %) of a thixotropic agent, and 0 to 30 wt % (more preferably 0.01 to 30 wt %) of an antioxidant.

The flux composition of the present invention can be used in, for example, the production of electronic components, electronic modules and printed circuit boards. The flux composition can be applied to the surface(s) to be soldered by any conventional technique including, for example, liquid spray techniques, liquid foaming techniques, pick and dip techniques and wave techniques or any other conventional technique capable of dispensing a liquid or semisolid onto a silicon die or substrate.

The flux composition of the present invention optionally further comprises a solder powder; wherein the flux composition is a solder paste. Preferably, the solder powder is an alloy selected from Sn/Pb, Sn/Ag, Sn/Ag/Cu, Sn/Cu, Sn/Zn, Sn/Zn/Bi, Sn/Zn/Bi/In, Sn/Bi and Sn/In (preferably wherein the solder powder is an alloy selected from 63 wt % Sn/37 wt % Pb; 96.5 wt % Sn/3.5 wt % Ag; 96 wt % Sn13.5 wt % Ag/0.5 wt % Cu; 96.4 wt % Sn/2.9 wt % Ag/0.5 wt % Cu; 96.5 wt % Sn/3 wt % Ag/0.5 wt % Cu; 42 wt % Sn/58 wt % Bi; 99.3 wt % Sn/0.7 wt % Cu; 91 wt % Sn/9 wt % Zn and 89 wt % Sn/8 wt % Zn/3 wt % Bi).

The solder paste preferably comprises: 1 to 50 wt % (more preferably 5 to 30 wt %, most preferably 5 to 15 wt %) of a fluxing complex formed by the combination of a carboxylic acid with an amine fluxing agent represented by formula I; and, 50 to 99 wt % of a solder powder. The solder paste can be compounded by conventional techniques, for example, by kneading and mixing the solder powder with the fluxing complex using conventional equipment for such operations.

The solder paste can be used in, for example, the production of electronic components, electronic modules and printed circuit boards. The solder paste can be applied to the surface(s) to be soldered by any conventional technique including, for example, printing the solder paste through a conventional solder mask using a solder printer or screen printer.

The amine fluxing agent used in the flux composition of the present invention can be prepared using conventional synthesis techniques well known to those of ordinary skill in the art.

The fluxing complex used in the flux composition of the present invention can be prepared by, for example: (a) combining an amine fluxing agent according to formula I with a carboxylic acid (see, e.g., Example 5); or (b) adding a carboxylic acid at some point during the preparation of an amine fluxing agent according to formula I. Preferably, the fluxing complex used in the flux composition of the present invention is prepared by combining an amine fluxing agent according to formula I with a carboxylic acid. Optionally, a fluxing agent according to formula I and a carboxylic acid can be combined in a solvent (e.g., 1,3-dioxolane) to facilitate the formation of the fluxing complex. The solvent can then be evaporated off leaving behind the fluxing complex.

The method of applying solder to an electrical contact of the present invention comprises: providing an electrical contact; providing a flux composition of the present invention; applying the flux composition to the electrical contact; providing a solder; melting the solder; and, displacing the flux composition applied to the electrical contact with the molten solder; wherein the molten solder makes physical contact with the electrical contact and bonds to the electrical contact. In the method, the molten solder desirably comes into intimate contact with the electrical contact to facilitate formation of a metallic bond between the solder material and the electrical contact, providing a good mechanical and electrical bond between the solder and the electrical contact. Any conventional soldering technique can be used in the method of the present invention. For example, a soldering bit or iron can be used to heat the electrical contact and the solder to a temperature above the melting point temperature for the solder. A soldering bath can be used, wherein solder in a liquid state is transferred to the electrical contact through immersion of the electrical contact into the molten solder. Conventional wave soldering techniques can be implemented. Also, reflow soldering techniques can also be used, wherein solder previously deposited onto a second electrical contact is brought into proximity with the first electrical contact and heated to a temperature above the melting point temperature of the solder, wherein the solder melts and reflows, coming into contact with both the first electrical contact and the second electrical contact, forming an electrical contact between the first electrical contact and the second electrical contact.

The method of applying solder to an electrical contact of the present invention can optionally be part of a flip chip soldering process, wherein a semiconductor chip is mounted onto a printed circuit board, wherein the semiconductor chip comprises a plurality of first electrical contacts and wherein the printed circuit board comprises a plurality of second electrical contacts. In such flip chip method, the flux composition of present invention is applied to either one, or both, of the plurality of first electrical contacts and the plurality of second electrical contacts to facilitate solder bonding of the plurality of first electrical contacts to the plurality of second electrical contacts to form electrical inter connects. Preferably, the flip chip solder process further comprises an under fill step wherein a thermosetting resin is provided to encapsulate the electrical inter connects. Most preferably, the thermosetting resin is an epoxy resin.

Some embodiments of the present invention will now be described in detail in the following Examples.

Example 1

Synthesis of Amine Fluxing Agent

A 2,6-diamino-2,5,6-trimethylheptan-3-ol amine fluxing agent was prepared using the following procedure. First, a 2,5,6-trimethyl-2,6-dinitroheptan-3-ol intermediate was prepared using the following synthesis method

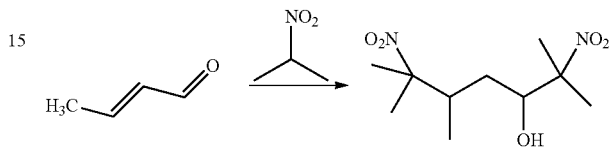

Specifically, a three neck round bottom flask was equipped with a stir bar, a thermocouple, a dropping funnel capped with a nitrogen inlet and a condenser. The flask was then charged with 2-nitropropane (50 g, 0.56 mols, 5.0 equivalents) and a catalytic amount of 1,8-diazabicyclo[5.4.0]undec-7-ene. The contents of the flask were then stirred under nitrogen for thirty minutes. Then crotonaldehyde (7.9 g, 9.2 mL, 0.112 moles, 1.0 equivalent) was added to the flask drop-wise over a period of twenty minutes. The contents of the flask were then stirred under nitrogen for 5-6 hours, during which a white solid was observed to precipitate from the solution. At this point, GC analysis showed the absence of any crotonaldehyde in the reaction mixture. The contents of the flask were allowed to stir overnight under nitrogen. The precipitate was then vacuum filtered from the solution and was washed thoroughly with water yielding a white solid. The intermediate solid was air dried, followed by vacuum drying at 45° C. The total yield of the desired intermediate dinitro alcohol was 72% (27.8 g). Nuclear magnetic resonance testing ("NMR") and liquid chromatography ("LC") showed that the intermediate was >99% pure.

Second, the product 2,6-diamino-2,5,6-trimethylheptan-3-ol amine fluxing agent was then prepared from the intermediate dinitro alcohol using the following synthesis method

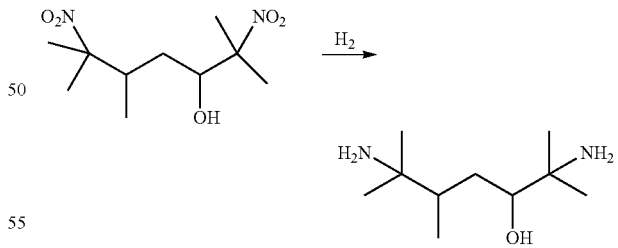

Specifically, 25 g of the intermediate dinitro alcohol was dissolved in 200 mL methanol with 14.2 g of RaNi 3111 as a catalyst. The mixture was then hydrogenated in an autoclave at 60° C. under 4,137 kPa (600 psi) of hydrogen pressure. After workup which included filtration of the catalyst and removal of methanol, 11 g (59% yield) of a low viscosity liquid product was obtained. NMR and gas chromatograph-mass spectroscopy ("GC-MS") analysis confirmed the presence of the desired product 2,6-diamino-2,5,6-trimethylheptan-3-ol amine fluxing agent. Chemical ionization mass spectroscopy (CI-MS) showed [M+H]=189 and GC analysis showed that the purity of the product to be 94%. The boiling point of the material was 125° C. to 135° C. at 0.68 kPa (5.1 torr). $^{13}$C NMR (CDCl$_3$): δ 16.8, 25.2, 27.9, 30.8, 34.7, 42.2, 51.8, 52.8 and 77.3 ppm.

Example 2

Synthesis of Amine Fluxing Agent

A 2,6-diamino-2,6-dimethyl-5-phenylheptan-3-ol amine fluxing agent was prepared using the following procedure. First, a 2,6-dimethyl-2,6-dinitro-5-phenylheptan-3-ol intermediate was prepared using the following synthesis method

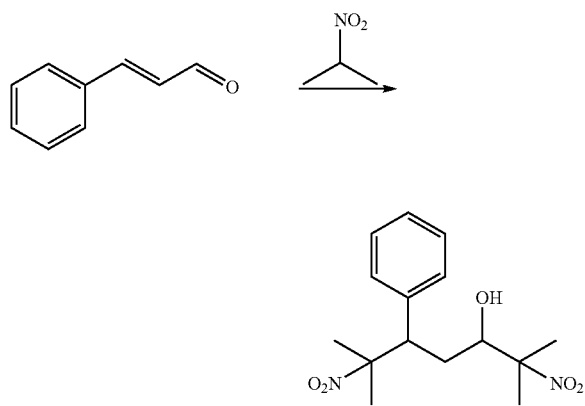

Specifically, a three neck round bottom flask was equipped with a stir bar, a thermocouple, a dropping funnel capped with a nitrogen inlet and a condenser. The flask was then charged with 2-nitropropane (101.1 g, 1.14 mols, 6.0 equivalents) and a catalytic amount of 1,8-diazabicyclo[5.4.0]undec-7-ene ("DKU"). The contents of the flask were then stirred under nitrogen for twenty minutes. Then trans-cinnamaldehyde (25.0 g, 0.19 moles, 1.0 equivalent) was added to the flask drop-wise over a period of twenty minutes. During the addition of the trans-cinnamldehyde, an exotherm of approximately 22° C. was observed. Following the complete addition of the trans-cinnamaldehyde, the flask contents were heated to 50° C. and maintained at that temperature for 4 hours. The mixture was then allowed to cool to room temperature. When the flask contents reached 36.8° C., a pale yellow solid formed out of the solution. The flask contents were then filtered through a Buchner funnel and the recovered intermediate diamino alcohol powder was washed thoroughly with pentane and ether. The intermediate diamino alcohol powder was then left to dry under vacuum for 1 hour. The total yield of the desired diamino alcohol intermediate was 62% (36 g). NMR analysis showed that the diamino alcohol intermediate was >99% pure. $^1$H NMR (CDCl$_3$): δ 1.45-2.27 (m, 15H), 3.52-3.54 (m, 1H), 3.67-3.74 (m, 1H), 7.17-7.34 (m, 5H). $^{13}$C NMR (CDCl$_3$): δ 20.8, 22.4, 23.2, 25.8, 31.3, 50.3, 72.9, 91.5, 91.6, 128.1, 128.7, 129.4, 136.6 ppm.

Second, the product 2,6-diamino-2,6-dimethyl-5-phenylheptane-3-ol amine fluxing agent was then prepared from the dinitro alcohol intermediate using the following synthesis method

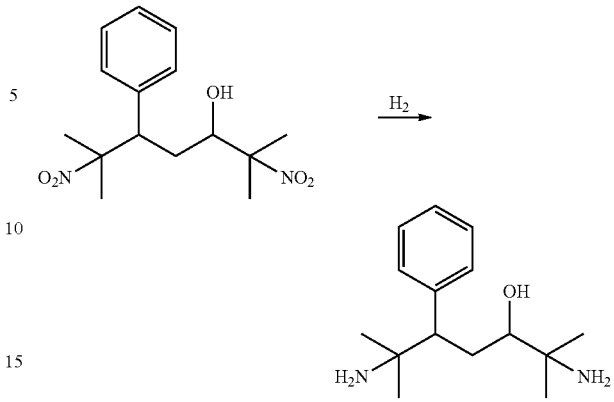

Specifically, 50 g of the dinitro alcohol intermediate was dissolved in 300 mL methanol with 24.3 g of RaNi 3111 as a catalyst. The mixture was then hydrogenated in an autoclave at 60° C. under 4137 kPa (600 psi) of hydrogen pressure. After workup which included filtration of the catalyst and removal of methanol, 40 g (68% yield) of a high viscosity liquid product was obtained. NMR and gas chromatograph-mass spectroscopy ("GC-MS") analysis confirmed the presence of the desired product 2,6-diamino-2,6-dimethyl-5-phenylheptane-3-ol amine fluxing agent. Chemical ionization mass spectroscopy (CI-MS) showed [M+H]=251 and GC analysis showed that the purity of the product to be 78% straight from the autoclave. The rest of the material present appeared to be the mono adduct obtained from the reversal of the Henry reaction. The product was then purified to 96.2% purity by vacuum distillation. The boiling point of the purified product was determined to be 150° C. to 160° C. at 0.67 kPa (5.0 torr). $^1$H NMR (CDCl$_3$): δ 0.91-0.99 (m, 12H), 1.67-1.81 (m, 3H), 2.71-2.76 (m, 2H), 7.08-7.23 (m, 5H). $^{13}$C NMR (CDCl$_3$): δ 24.6, 27.9, 28.3, 29.8, 31.6, 51.8, 52.6, 54.2, 75.9, 126.3, 127.8, 129.4, 142.0 ppm.

Example 3

Synthesis of Amine Fluxing Agent

An amine fluxing agent having the formula

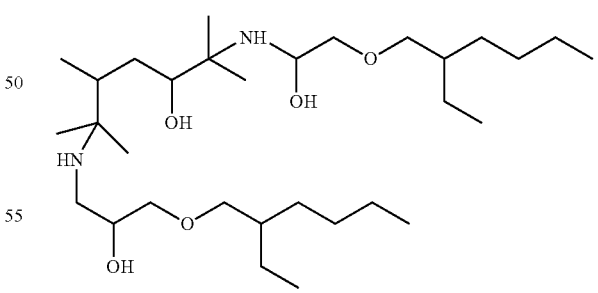

was prepared using the following procedure. Specifically, into a reaction vessel with a stir bar, (0.05 mol) of the product of Example 1 was added. The reaction vessel was then placed on a hotplate with magnetic stirring capability. The reaction vessel was then inerted with nitrogen and (0.1 mol) of 2-ethylhexyl glycidyl ether (available from Momentive Performance Materials) was then added to the reaction vessel at ambient temperature, with stirring. The set point temperature on the hot plate was then raised to 75° C. and the contents of the reaction vessel were allowed to continue stirring for two (2) hours. The set point temperature of the hot plate was then raised to 140° C. and the contents of the reaction vessel were allowed to continue stirring for two (2) more hours. The set point temperature of the hot plate was then reduced to 80° C. and a vacuum was pulled on the reaction vessel, reducing the pressure in the vessel to 30 mm Hg. The contents of the reaction vessel were allowed to continue stirring under these conditions for another two (2) hours to provide the product fluxing agent. The percent weight loss from the product fluxing agent upon heating to 250° C. was measured by thermogravimetric analysis (TGA) using a temperature ramp of 10° C./min starting at 25° C. The measured weight loss (WL) for the product fluxing agent was 9 wt %.

Example 4

Synthesis of Amine Fluxing Agent

An amine fluxing agent having the formula

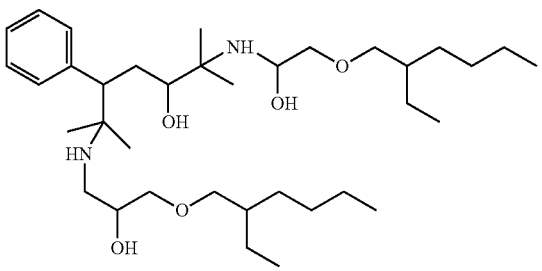 [SMILES: CCCCC(CC)COCC(O)CNC(C)(C)C(CC(O)C(C)(C)NC(O)COCC(CC)CCCC)c1ccccc1]

was prepared using the following procedure. Specifically, into a reaction vessel with a stir bar, (0.05 mol) of the product of Example 2 was added. The reaction vessel was then placed on a hotplate with magnetic stirring capability. The reaction vessel was then inerted with nitrogen and (0.1 mol) of 2-ethylhexyl glycidyl ether (available from Momentive Performance Materials) was then added to the reaction vessel at ambient temperature, with stirring. The set point temperature on the hot plate was then raised to 75° C. and the contents of the reaction vessel were allowed to continue stirring for two (2) hours. The set point temperature of the hot plate was then raised to 140° C. and the contents of the reaction vessel were allowed to continue stirring for two (2) more hours. The set point temperature of the hot plate was then reduced to 80° C. and a vacuum was pulled on the reaction vessel, reducing the pressure in the vessel to 30 mm Hg. The contents of the reaction vessel were allowed to continue stirring under these conditions for another two (2) hours to provide the product fluxing agent. The percent weight loss from the product fluxing agent upon heating to 250° C. was measured by thermogravimetric analysis (TGA) using a temperature ramp of 10° C./min starting at 25° C. The measured weight loss (WL) for the product fluxing agent was 5 wt %.

Example 5

Preparation of Fluxing Complex

An amine fluxing agent (4 g) prepared according to the procedure set forth in Example 3 was hand mixed with 1,4-dihydroxy-2-naththoic acid (0.37 g) in 1,3-dioxolane (1.5 g) under ambient conditions to form a fluxing complex having an amine fluxing agent amine nitrogen to carboxylic acid acid content (—COOH) equivalent ratio of about 2:1. The 1,3-dioxolane was removed from the fluxing complex by heating to 80° C. for thirty minutes.

The percent weight loss from the fluxing complex upon heating to 230° C. was then measured by thermogravimetric analysis (TGA) using a temperature ramp of 10° C./min starting at 25° C. The measured weight loss (WL) for the fluxing complex was 20.2 wt %.

Example 6

Preparation of Fluxing Complex

An amine fluxing agent (4 g) prepared according to the procedure set forth in Example 4 was hand mixed with 1,4-dihydroxy-2-naththoic acid (0.37 g) under ambient conditions using a spatula to form a fluxing complex having an amine fluxing agent amine nitrogen to carboxylic acid acid content (—COOH) equivalent ratio of 1.8:1.

The percent weight loss from the fluxing complex upon heating to 250° C. was measured by thermogravimetric analysis (TGA) using a temperature ramp of 10° C./min starting at 25° C. The measured weight loss (WL) for the fluxing complex was 13.6 wt %.

Example 7

Evaluation of Fluxing Capability

The fluxing capability of the fluxing complex prepared according to Example 6 was evaluated using the following procedure. A copper coupon was used as an electrical contact to be soldered. A small drop of the fluxing complex prepared according to Example 6 was dispensed onto the surface to be soldered of the copper coupon. Four 0.381 mm diameter balls of a lead-free solder (95.5 wt % Sn/4.0 wt % Ag/0.5 wt % Cu) were placed into the drop of fluxing complex on the copper coupon. The melting range of the lead-free solder used was 217 to 221° C. The copper coupon was then placed on a hotplate that was preheated to 145° C. and held there for two (2) minutes. The copper coupons were then placed on another hotplate preheated to 260° C. and held there until the solder reached reflow conditions. The copper coupon was then removed from the heat and evaluated by (a) the extent of fusion and coalescence of the originally placed four solder balls, (b) the size of the resulting coalesced solder to assess the flow and spread and (c) the bonding of the solder to the surface of the copper coupon. The fluxing capability of the fluxing complex was determined to be a 4 on a scale of 0 to 4, wherein:

0=no fusion between solder drops and no solder bonding to copper coupon;

1,2 =partial to complete fusion between solder drops, but no solder bonding to copper coupon;

3=complete fusion between solder drops, but minimal solder spread and flow;

4=complete fusion between solder drops, good solder spread and flow over surface of copper coupon and solder bonding to the copper coupon.

We claim:

1. A flux composition comprising, as initial components:
a carboxylic acid; and,
an amine fluxing agent represented by formula I:

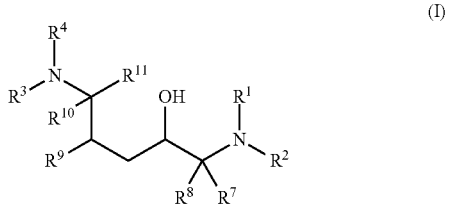

wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group.

2. The flux composition of claim 1, wherein the carboxylic acid is selected from the group consisting of a $C_{8-80}$ aliphatic mono carboxylic acids; $C_{2-20}$ aliphatic dicarboxylic acids; $C_{6-20}$ aromatic carboxylic acids; and, mixtures thereof.

3. The flux composition of claim 2, wherein the carboxylic acid is selected from the group consisting of octanoic acid; nonanioc acid; undecanoic acid; dodecanoic acid; tridecanoic acid; tetradecanoic acid; pentadecanoic acid; hexadecanoic acid; heptadecanoic acid; stearic acid; hydroxy stearic acid; oleic acid; linoleic acid; α-linolenic acid; icosanoic acid; oxalic acid; malonic acid; succinic acid; malic acid; glutaric acid; adipic acid; pimelic acid; suberic acid; benzoic acid; phthalic acid; isophthalic acid; terephthalic acid; hemimellitic acid; trimellitic acid; trimesic acid; mellophanic acid; prehnitic acid; pyromellitic acid; mellitic acid; toluic acid; xylic acid; hemellitic acid; mesitylene acid; prehnitic acid; cinnamic acid; salicylic acid; benzoic acid; naphthoic acid; phenolphthalin; diphenolic acid and mixtures thereof.

4. The flux composition of claim 1, wherein the flux composition exhibits a fluxing agent amine nitrogen to carboxylic acid acid content (—COOH) equivalent ratio of 1:1 to 20:1.

5. The flux composition of claim 1, wherein the substitutions in the substituted $C_{1-80}$ alkyl group and the substituted $C_{7-80}$ arylalkyl group, from which $R^1$, $R^2$, $R^3$ and $R^4$ are selected, are selected from at least one of an —OH group, an —$OR^5$ group, a —$COR^5$-group, a —$COR^5$ group, a —C(O)$R^5$ group, a —CHO group, a —$COOR^5$ group, an —OC(O)$OR^5$ group, a —S(O)(O)$R^5$ group, a —S(O)$R^5$ group, a —S(O)(O)$NR^5_2$ group, an —OC(O)$NR^6_2$ group, a —C(O)$NR^6_2$ group, a —CN group, a —N($R^6$)-group and a —$NO_2$ group; wherein $R^5$ is selected from a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group; wherein $R^6$ is selected from a hydrogen, a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group.

6. The flux composition of claim 1, wherein $R^1$, $R^2$, $R^3$ and $R^4$ are independently selected from a hydrogen, a —$CH_2CH(OH)R^{18}$ and a —$CH_2CH(OH)CH_2$—O—$R^{18}$ group; wherein $R^{18}$ is selected from a hydrogen, a $C_{1-28}$ alkyl group, a $C_{3-28}$ cycloalkyl group, a $C_{6-28}$ aryl group, a $C_{7-28}$ arylalkyl group and a $C_{7-28}$ alkylaryl group; wherein $R^7$ and $R^8$ are both a methyl group; wherein $R^{10}$ and $R^{11}$ are both a methyl group; and, wherein $R^9$ is selected a methyl group and a phenyl group; and wherein zero to three of $R^1$, $R^2$, $R^3$ and $R^4$ is(are) hydrogen.

7. The flux composition of claim 3, wherein zero to three of $R^1$, $R^2$, $R^3$ and $R^4$ is(are) hydrogen.

8. The flux composition of claim 1, further comprising, as initial components:
0 to 95 wt % of a solvent,
0 to 30 wt % of a thickening agent,
0 to 30 wt % of a thixotropic agent, and
0 to 30 wt % of an antioxidant.

9. The flux composition of claim 1, further comprising: a solder powder.

10. A method of applying solder to an electrical contact, comprising:
providing an electrical contact;
providing a flux composition according to claim 1;
applying the flux composition to the electrical contact;
providing a solder;
melting the solder; and,
displacing the flux composition applied to the electrical contact with the molten solder;
wherein the molten solder makes physical contact with the electrical contact and bonds to the electrical contact.

* * * * *